US012779188B2

(12) United States Patent
Bain

(10) Patent No.: US 12,779,188 B2
(45) Date of Patent: Nov. 3, 2026

(54) DILATATION DEVICE INCORPORATING INFLATABLE BALLOON

(71) Applicant: Growth Armor, LLC, Wilmington, DE (US)

(72) Inventor: Michael A. Bain, Costa Mesa, CA (US)

(73) Assignee: Growth Armor, LLC, Wilmington, DE (US)

( * ) Notice: Subject to any disclaimer, the term of this patent is extended or adjusted under 35 U.S.C. 154(b) by 1263 days.

(21) Appl. No.: 17/655,761

(22) Filed: Mar. 21, 2022

(65) Prior Publication Data

US 2023/0293863 A1 Sep. 21, 2023

(51) Int. Cl.
*A61M 29/02* (2006.01)

(52) U.S. Cl.
CPC ......... *A61M 29/02* (2013.01); *A61M 2205/33* (2013.01); *A61M 2205/3331* (2013.01); *A61M 2205/8206* (2013.01); *A61M 2205/8237* (2013.01)

(58) Field of Classification Search
CPC .. A61M 29/00; A61M 29/02; A61M 2205/33; A61M 2205/3331; A61M 2205/8206; A61H 2023/002; A61H 2201/0103; A61H 2201/1238; A61H 2201/5071; A61H 2201/5084; A61H 19/00; A61H 19/32; A61H 19/40; A61H 19/44; A61H 19/50; A61H 21/00; A61H 2210/1067; A61H 2210/1475; A63B 23/20; A63B 2225/62
See application file for complete search history.

(56) References Cited

U.S. PATENT DOCUMENTS

| | | | | |
|---|---|---|---|---|
| 5,415,635 A * | 5/1995 | Bagaoisan | A61M 25/1029 604/101.05 |
| 9,861,800 B2 * | 1/2018 | Alexander | A61M 29/00 |
| 2009/0111671 A1 * | 4/2009 | Campbell | A61M 25/10 604/509 |
| 2010/0082057 A1 * | 4/2010 | Borkon | A61M 29/02 606/193 |
| 2011/0295302 A1 | 12/2011 | Mohl | |
| 2012/0215141 A1 | 8/2012 | Peddicord | |

(Continued)

*Primary Examiner* — Rachel T Sippel
*Assistant Examiner* — Gwynneth L Howell
(74) *Attorney, Agent, or Firm* — Stetina Garred Brucker & Newboles

(57) ABSTRACT

Superior dilatation devices and methods of using such devices are contemplated which are effective for providing enhanced levels of sexual stimulation as well as enhancing the treatment or amelioration of conditions which may be treated with dilatation, such as vaginismus and other forms of dyspareunia, pelvic floor dysfunction, and certain other forms of incontinence. By positioning a tubular balloon around the shaft of a conventional rigid dilatation device, providing a reservoir inside the body of the device containing an inflation fluid like helium gas, and using a pump to transfer the inflation between the two, the balloon may be inflated and deflated repeatedly and on command. Through particular control systems, potentially including biofeedback elements and arrangements of multiple balloon lumens, the inflation/deflation sequence may be customized and optimized to produce an enhanced stimulative or treatment effect.

15 Claims, 3 Drawing Sheets

(56) References Cited

U.S. PATENT DOCUMENTS

| | | | | |
|---|---|---|---|---|
| 2013/0233321 | A1* | 9/2013 | Singh | A61M 16/0434 128/207.15 |
| 2014/0088468 | A1 | 3/2014 | Murison | |
| 2014/0336452 | A1 | 11/2014 | Shahoian et al. | |
| 2020/0337941 | A1* | 10/2020 | Leivseth | A61H 23/02 |
| 2021/0177691 | A1 | 6/2021 | Shahoian et al. | |
| 2022/0087806 | A1* | 3/2022 | Shaker | A63B 23/20 |

* cited by examiner

DILATATION DEVICE INCORPORATING INFLATABLE BALLOON

CROSS-REFERENCE TO RELATED APPLICATIONS

Not Applicable

STATEMENT RE: FEDERALLY SPONSORED RESEARCH/DEVELOPMENT

Not Applicable

BACKGROUND

1. Technical Field

The present disclosure relates generally to the field of dilatation devices for therapeutic and recreational purposes. More particularly, the present disclosure relates to superior dilatation devices and methods of using such devices which are effective for providing enhanced levels of sexual stimulation as well as enhancing the treatment or amelioration of conditions which may be treated with dilatation, such as vaginismus and other forms of dyspareunia, pelvic floor dysfunction, and certain other forms of incontinence.

2. Related Art

There are a number of reasons for which an individual may utilize a device configured for insertion into vagina or anus. Medically, there are a number of disorders that involve the pelvic area, including of the bladder, vagina, pelvic floor muscle, rectum and cervix, for which insertion of devices for therapeutic treatment is a common method of treatment.

The pubococcygeal muscle, commonly called the pelvic floor muscle, is responsible for holding all the pelvic organs within the pelvic cavity. The pelvic floor muscle consists of a deep muscle layer and a superficial muscle layer that work together to keep the pelvic organs healthy and in good working order. The muscle is suspended at the base of the pelvis and wraps around the vagina and rectum. The pelvic floor muscles may become damaged or weakened through childbirth, lack of use, aging, illness, or as the collateral result of surgical procedures. One of the symptoms related to a weakening of these muscles is urinary incontinence.

Other pelvic disorders include chronic pelvic pain and vulvodynia (pelvic muscle dysfunction), which may sometimes be experienced by young adult women. These disorders may be caused by involuntary contractions (spasms) of the levator ani and perineal muscles. This condition, sometimes referred to as vaginismus or pelvic floor tension myalgia, may be accompanied by difficult and painful penetration of the vagina, often resulting in pain and other difficulties which substantially reduce a woman's quality of life, not only with regard to the participating in and enjoyment of penetrative sexual intercourse, but also in other facts of life, such as in the use of menstrual products such as tampons or during routine procedures such as the use of speculums during gynecological examinations.

Dilatation devices are commonly prescribed for the treatment of such conditions, and generally include products such as vaginal dilators and Kegel exercisers. Similarly, dilatation devices for insertion into the anus may also be prescribed, for example, in order to aid in treatment of conditions such as anal stenosis, where treatment involves progressive stretching and acclimation of the rectum to an ideal size to improve comfort and function following anorectal procedures, such as following surgeries on the prostate or for hemorrhoids.

Similarly, dilatation devices are also used for the enhancement of sexual pleasure, and in this context, such devices generally are referred to as sex toys. There may also be substantial overlap between the structure and functionality of devices adapted for therapeutic and recreational uses, and in many cases, especially when a pelvic disorder may directly impact the ability to enjoy sexual intercourse and pleasure, a single device may be utilized for both purposes. Many types of sex toys are known. Some of the most popular sex toys are designed for vaginal or anal insertion, and include items such as dildos, prostate stimulators, anal plugs, etc. Many of these devices may also include other stimulatory elements, such as vibrating or rotating functionalities.

Existing dilatation devices suffer from a number of deficiencies, however. For example, conventional treatment of vaginismus or anal stenosis typically entails the progressive insertion of a progressively larger sequence of dilators until the vagina or anus becomes acclimated to the desired size. It is therefore desirable to have improved dilatation devices which may, for example, provide adaptive forms of dilation therapies, potentially even taking into consideration biofeedback mechanisms, in order to assist in user comfort and to eliminate the requirement for the use of a series of dilators. Likewise, similar deficiencies may exist in the field of sex toys, and consequently, overall sexual pleasure may be enhanced the application of similar techniques to produce improved sex toys for insertion.

BRIEF SUMMARY

To solve these and other problems, an enhanced dilatation device is contemplated in which technologies pioneered in catheterized balloon techniques such as angioplasty, and other enlargement or disocclusion procedures may be applied to conventional devices in novel ways. In particular, a tubular balloon may be positioned around the shaft of a conventional rigid dilatation device (e.g. vaginal or anal dilators, penetrative sex toys (dildos), pelvic floor/Kegel trainers and stimulators, etc.), with a reservoir inside the body of the dilatation device filled with an inflation fluid such as helium gas. Via the action of a pump which transfers the inflation fluid to and from the internal fluid reservoir along an inflation fluid pathway to an internal lumen within the balloon, which is formed of a resilient but flexible material, may be seen to inflate and deflate, resulting in enhanced and controllable dilatation beyond that provided by the insertion of the rigid dilatation device alone. Furthermore, it is contemplated that enhanced control mechanisms may enable the inflation and deflation of the balloon portion of the device according to various criteria. For example, an accelerometer may be embedded within the device to monitor the direction and velocity of the device, which may enable the balloon portion to be inflated during insertion of device into the vagina or anus at a rate to matches the speed of insertion in order to produce a consistent enhanced dilatation effect regardless of the frequency of sequential insertion and retraction cycles. Similarly, the accelerometer may also detect the retraction of the device and the speed of retraction, and to correspondingly deflate the balloon portion in accordance with the rate of retraction of the device, so that the device can be more easily retracted and will thereafter be in the deflated configuration in time for the subsequent insertion. Further, because of the adjustability of the inflated and deflated state, a single device may be utilized where in the past multiple prior art devices may have been required.

According to one exemplary embodiment, the enhanced dilatation device may comprise a rigid elongated member having a proximal end, distal end, and a shaft region therebetween, a sheath secured to and at least partially enclosing at least a portion of the exterior of the shaft region, the sheath having an outer surface and an inflation lumen, the inflation lumen being transitionable between at least a deflated configuration and an inflated configuration, wherein transitioning of the inflation lumen to the inflated configuration is operative to cause an inflation portion of the outer surface to expand away from the exterior of the shaft region, and wherein transitioning of the inflation lumen to the deflated configuration is operative to cause the inflation portion of the outer surface to retract towards the exterior of the shaft region, a reservoir operative to contain inflation fluid, a conduit defining an inflation fluid pathway between the reservoir and the inflation lumen, a pump associated with the inflation fluid pathway, the pump being operative to regulate the flow of inflation fluid between the reservoir and the inflation lumen, a net flow of inflation fluid from the reservoir into the inflation lumen being associated with the transition of the inflation lumen to the inflated configuration, and a net flow of inflation fluid from the inflation lumen into the reservoir being associated with the transition of the inflation lumen to the deflated configuration, and a control unit being operative to control at least the operation of the pump. According to more particular embodiments of such enhanced dilatation devices, the reservoir may be enclosed within the rigid elongated member.

An enhanced dilatation device may also comprise an accelerometer for detecting motion of the enhanced dilatation device. The control unit may be configured to operate the pump so as to cause transition of the inflation lumen to or from the inflated or deflated configuration in response to detection of motion of the enhanced dilatation device by the accelerometer. The accelerometer may also be configured to detect a direction of motion of the enhanced dilatation device along a longitudinal axis of the rigid elongated member, and wherein the control unit is configured to operate the pump so as to cause the inflation lumen to transition to the inflated configuration in response to a detection of motion along the longitudinal axis in the direction of the distal end, and to operate the pump so as to cause the inflation lumen to transition to the deflated configuration in response to a detection of motion along the longitudinal axis in the direction of the proximal end. According to a more particular embodiment, the accelerometer may also be further configured to detect a velocity of the enhanced dilatation device along a longitudinal axis of the rigid elongated member, and wherein the control unit is further configured to operate the pump so as to control the rate of transition of the inflation lumen between the inflated and deflated configurations as a function of the detected velocity.

An enhanced dilatation device may also comprise a pressure sensor for determining a pressure within the inflation lumen. The control unit may be configured to operate the pump in response to determination of pressures within the inflation lumen by the pressure sensor. According to one particular embodiment, the control unit may be configured to operate the pump so as to cause the inflation lumen to transition between the inflated and deflated configurations in response to a determination that the pressure within the inflation lumen is above or below one or more predefined pressure levels. It is also contemplated that according to further embodiments, the control unit may be configured to operate the pump in response to determinations of pressure changes within the internal lumen in order to maintain a consistent internal volume of the inflation lumen.

According to certain other embodiments, the enhanced dilatation device is also contemplated as further comprising a stimulatory module adapted to provide additional stimulation. In certain contemplated embodiments in particular, the stimulatory module may comprise a vibrational element.

Certain embodiments of the herein disclosed enhanced dilatation devices are further contemplated as comprising a power supply for supplying power to at least the pump, which may be, for example, a rechargeable battery. The herein disclosed enhanced dilatation devices are also comprising as including a pressure release valve associated with the inflation lumen. According to more specific embodiments disclosed herein, the inflation fluid may be comprised of helium.

According to further contemplated embodiments, the enhanced dilatation device may comprise two or more inflation lumens. Each of the two or more inflation lumens may be independently transitionable between at least a deflated configuration and an inflated configuration.

It is also contemplated that in certain embodiments of the enhanced dilatation device, the control unit may be configured to receive inputs from a user to control the functionality of the enhanced dilatation device. The control unit, in more specific embodiments, may comprise as wireless receiver and/or transmitter for permitting a user to wirelessly control the functionality of the enhanced dilatation device.

The present disclosure will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which.

Common reference numerals are used throughout the drawings and the detailed description to indicate the same elements.

DETAILED DESCRIPTION

According to various aspects of the present disclosure, new and improved dilatation devices are contemplated in which catheterized balloon technologies are incorporated to produce new and improved effects. A tubular inflatable balloon may be placed around the shaft of a conventional rigid device for vaginal or anal insertion, such as a dildo, a dilator, or a pelvic floor relaxer. A reservoir may be included inside the body of the device and filled with helium gas or another suitable fluid for inflating the balloon. A pump can be positioned along an inflation fluid pathway which connects the reservoir to an internal lumen within the balloon, which functions to transfer the inflation fluid to inflates and deflate the balloon, resulting in an enhanced dilatation effect when the balloon is inflated. Due to the configuration of the device, control mechanisms are possible to enable the automatic or manual inflation and deflation of the balloon portion of the device. In an exemplary embodiment, an accelerometer embedded within the device monitors the direction and velocity of its travel, which results in the balloon portion being inflated during insertion of device into the vagina or anus at a speed which matches speed of insertion. The accelerometer also detects the retraction of the device and the speed of retraction, and causes the balloon portion to be deflated in accordance with the measured speed of retraction of the device, aiding in smooth retraction while maintaining an optimized dilatation effect as well as ensuring the device will be prepared for the next insertion. Likewise, the parameters of the inflation pressure or velocity may also be customized by the user to allow for different levels or qualities of dilatation with a single device. Other biofeedback mechanics are also contemplated wherein, for example, pressure sensors may allow for dynamic feedback so as to optimize the balloon inflation parameters to result in enhanced dilatation effects.

Figure 1:
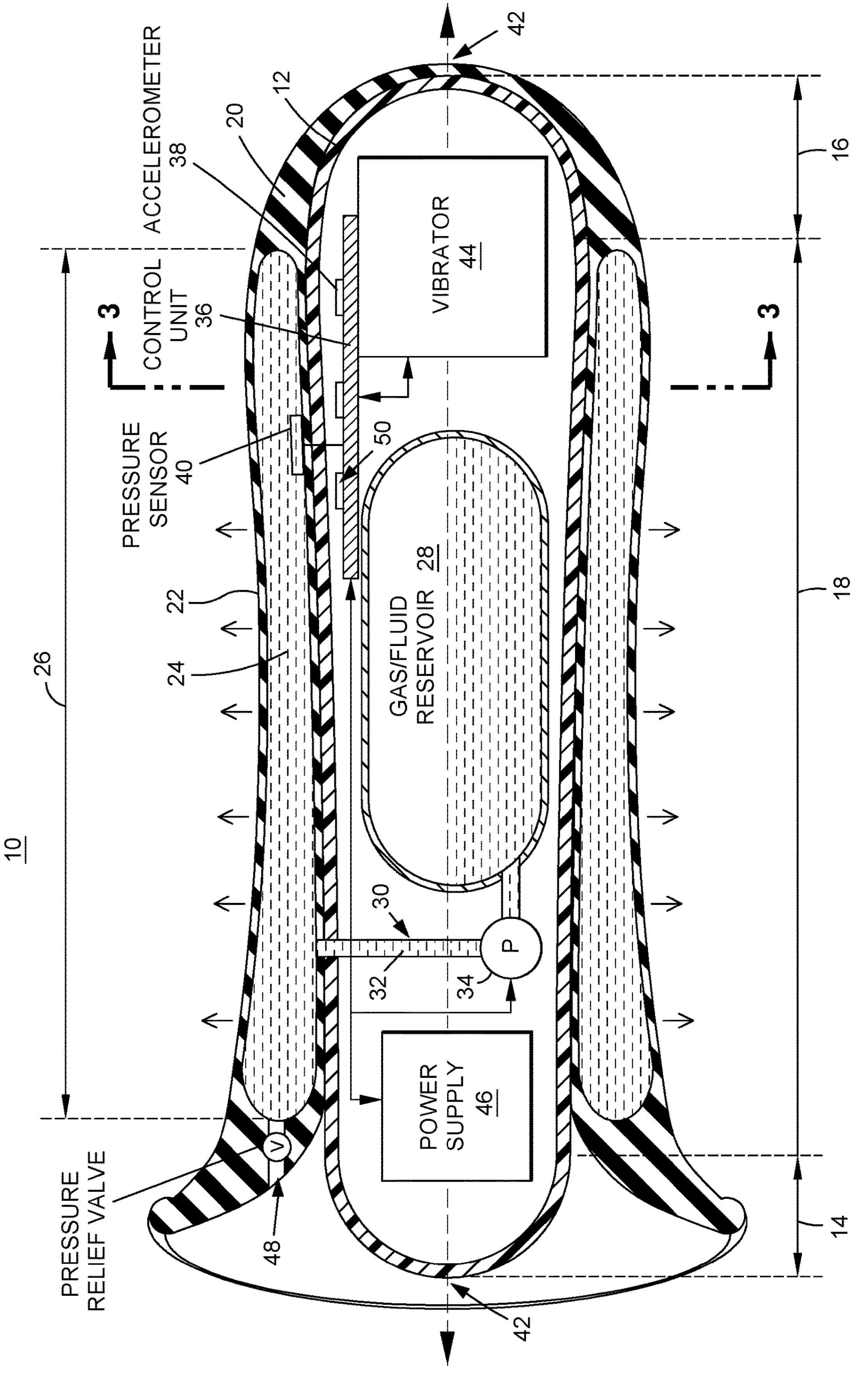
FIG. 1 is a side cutaway view illustrating an enhanced dilatation device according to a first exemplary embodiment of the present disclosure.

Turning now to FIG. 1, a side cutaway view illustrating an enhanced dilatation device according to a first exemplary embodiment of the present disclosure is shown. As may be seen, an enhanced dilatation device 10 may comprise a rigid elongate member 12 having a proximal end 14, a distal end 16, a shaft region 18 therebetween, and a sheath 20 secured to and at least partially enclosing at least a portion of the exterior of the shaft region 18.

The rigid elongate member 12 may be any type of rigid elongate member generally shaped and sized for insertion into a body cavity for use as a dilatation device or other form of sex toy. In particular, is it contemplated that the rigid elongate member 12 may, in the exemplary embodiment, be a generally linear ovoid shape, similar to many conventional dilator or dildo products currently offered for sale. It may be seen, however, that the shape, size, and exterior features of the rigid elongate member 12 may be substantially variable or customized, similar to the way that many conventional dilator or dildo products are also varied, including in size, shape, curvature, style, color, etc. For example, while in the illustrated embodiments the rigid elongate member 12 has a generally circular cross-section similar to many dilator and dildo products, other cross-sectional shapes are expressly contemplated as being within the scope and spirit of the present disclosure. The exact configuration of the rigid elongate member 12 is not necessarily to be limited, and as long as the enhanced dilation device 10 incorporating the rigid elongate member 12 is suitable for insertion by an individual for treatment of a pelvic condition or for the enhancement of sexual pleasure. Likewise, the exact material of the rigid elongate member 12 should not necessarily be limited to any particular material. For example, plastics, rubber, composites, metals, woods, glasses, ceramics, or any other material may be seen as suitable for use. It should be considered within the scope and spirit of the present disclosure. It should also be appreciated that the term "rigid" is not necessarily an absolute term, and that it is not necessary that the rigid elongate member 12 be totally rigid in the sense that it will not be able to flex or bend or deform. Rather, the term "rigid" in the rigid elongate member 12 it to be understood by way of comparison to the material of the sheath 20, in that the rigid elongate member 12 should be understood in context of the function of the core aspects of the disclosure, i.e. that it should be less flexible and less deformable than those material used by the certain portions of the sheath 20, that are expressly contemplated as being capable of flexing and deforming between a deflated and inflated configuration, in the fashion of a balloon expanding.

The rigid elongate member 12 is contemplated as having a proximal region 14 and a distal region 16 which may not necessarily be enclosed by the sheath 20. It is generally contemplated that the proximal region 14 will be the region which is manipulated or maintained in position during use of the device, while the distal region 16 will be the region which is inserted by the user, and as such, the two regions may differ in shape or configuration so as to assist in use, for example, by being flared in order to prevent undesired over-insertion, and potentially by being equipped with a handle in the case of a device meant for manual insertion, or attachment point for a handle or other form of fixation, such as a mounting element, which may enable the device to be used with a separately provided handle, or attached to a surface with a suction cup, or for use with a harness in order to enable use of the device as a prosthetic (e.g. in the manner of a strap-on dildo), or to permit interconnection of two or more enhanced dilation devices 10 for simultaneous use with a sexual partner or for simultaneous insertion of two separate enhanced dilation devices 10 in the vagina and rectum of a single individual. However, the exact form of the proximal region 14 is not necessarily limited in any such fashion, and configurations of the proximal region 14 other than those described herein should not be construed to limit the scope or spirit of the present disclosure.

Similarly, the distal region 16 may also be configured in a number of ways, without necessarily limiting the scope and spirit of the present disclosure. It is generally contemplated that the distal region 16 will generally somewhat resilient and streamlined, as this is the portion of the device which will primarily encounter resistance during the insertion of the enhanced dilation device 10, so a more streamlined form may assist in ease of insertion. However, there is no strict requirement as to form or material of the distal region 16. Likewise, it is conceivable that the enhanced dilation devices 10 may be reversible, in that both the proximal or distal regions 14, 16 may be configured to be interchangeable, or at least capable of being inserted, and as such there may not necessarily be a single defined proximal or distal regions 14, 16, but rather each end which is referred to in each fashion herein may change according to the manner in which the device is utilized, without departing from the scope and spirit of the present disclosure.

The shaft region 18 is contemplated as representing the region of the rigid elongate member 12 between the proximal and distal regions 14, 16. Similar to the above definitions, the shaft region 18 is likewise not necessarily strictly defined in form, and does not necessarily need to be generally linear and straight-walled in the manner pictured in the illustrated embodiments, but many also be curved, arcuate, undulate, otherwise irregularly shaped, without departing from the scope and spirit of the present disclosure.

The sheath 20 is contemplated as being secured to and at least partially enclosing at least a portion of the exterior of the shaft region 18. According to the exemplary embodiment, the sheath is contemplated as comprising one or more outer surfaces 22, one or more inflation lumens 24, and one or more inflation portions 26. As shown in the exemplary embodiment, the sheath 20 may cover the distal region 16 of the rigid elongate member 12 and may fully enclose the shaft region 18. However, it may be seen that the sheath 20 may not necessarily cover and enclose all or even most of the shaft region 18, nor entirely surround the perimeter of the rigid elongate member 12. For example, it may be seen that the distal region of the rigid elongate member 12 may be exposed in certain embodiments, and the sheath 20 may only be positioned over certain portions of the shaft region 18. The outer surface of the sheath 20 may typically be formed of a material which will not result in discomfort to the user when used, and may, in certain embodiments, be a flexible, stretchable material that is generally impermeable to the passage of gases or liquids, such as natural or synthetic rubbers, latex, or nylon. However, it may also be seen that other materials may be utilized which might not necessarily be required to be generally impermeable to the passage of gases or liquids, as long as the inflation lumen 24 is itself generally impermeable to the passage of gases or liquids, which may be achieved by the incorporation of a lining or coating on the surfaces thereof. Likewise, it is also contemplated that the sheath 20 and/or the outer surface thereof may be formed of multiple types or of materials or different configurations or thicknesses of a single material, for example, a more resilient, less deformable material may be utilized at regions which are not configured to deform substantially (e.g. the regions covering the distal region 16 in the illustrated embodiment), while a substantially more deformable material may be utilized at the inflation portions 26 where the outer surface 22 is configured to expand outwards during inflation of the inflation lumen 24.

The inflation lumen 24 and the inflation portion 26 are contemplated to function in coordination to cause the outer surface 22 at the inflation portion 26 to expand away from the exterior of the shaft region 18 at predetermined locations when the inflation lumen 24 is transitioned to the inflated configuration, and to likewise to cause those outer surface 22 at the inflation portion 26 to retract towards the exterior of the shaft region 18 when the inflation lumen 24 is transitioned to the deflated configuration. As may be seen, the structure of the inflation lumen(s) 24 and the inflation portion(s) 26 will generally dictate the form in which this will take. In the exemplary embodiment shown in FIG. 1, the inflation lumen 24 may be seen to entirely encircles the shaft region 18 such that there is only a single continuous inflation lumen 24 which extends along nearly the entire length of the shaft region 18, with the inflation portion representing substantially all of the outer surface 22 above the inflation lumen 24. Thus, it may be seen that when the inflation lumen 24 is inflated, the outer surface 22 will tend to expand outwards substantially equally in all directions, resulting in the effective cross-sectional diameter of the enhanced dilatation device 10 being essentially increased along in all dimensions along nearly the entirety of the shaft region 18 that constitutes the inflation portion 26. However, it may also be seen that different configurations of inflation lumen (s) 24 and inflation portion(s) 26 may result in different resultant shapes and sizes of the device when transitioned to the inflated state, and that such different configurations are expressly contemplated as being within the scope and spirit of the present disclosure. For example, it may be seen that by positioning inflation lumen(s) 24 or inflation portion(s) 26 at only particular locations around the shaft region 18, or by configuring such elements in different ways, the sheath 20 may be configured to only expand outwards at certain locations, or to expand outwards more substantially at certain locations compared to other locations. In this fashion, for example, it may be seen that it would be possible to achieve many different particularized expansion effects, and that such effects may be more or less beneficial according to the particular purpose and configuration of the enhanced dilatation device 10. For example, it may be desired to for the device to expand more substantially along one plane and less substantially along another plane, or at certain distances down the shaft region 18 compared to others, so as to achieve, for example, an undulate effect which may result in enhanced sexual pleasure. All of these different configurations are to be considered within the scope of and spirit for the present disclosure.

The enhanced dilatation device 10 is further contemplated to include a reservoir 28, a conduit 30 defining an inflation fluid pathway 32 between the reservoir 28 and the inflation lumen 24, and a pump 34 associated with the inflation fluid pathway, the pump being operative to regulate the flow of inflation fluid between the reservoir 28 and the inflation lumen. In the exemplary embodiment, the reservoir 28 is enclosed within the rigid elongated member 12. However, it may be seen that in other embodiments, the reservoir 28 may not necessarily be enclosed within the rigid elongated member 12, but may be a distinct component, for example, integrated with a separate element which is tethered to the remainder of the enhanced dilatation device 10. Further, it may be seen that according to still other embodiments the reservoir 28 may not be entirely enclosed within the rigid elongated member 12, but may be only partially enclosed within, for example, as a cartridge or canister attached to the remainder of the enhanced dilatation device, which may be preferable in embodiments where it may be desirable to remove or replace the reservoir 28. Such cartridges or canisters may be, for example, similar or identical in appearance and configuration to conventional threaded compressed gas cartridges used in many conventional applications (e.g. $CO_2$ canisters for use in chargers for whip cream dispensers and carbonated beverage dispensers in the food service industry, or liquid nitrogen cartridges for use with cryoprobes or cryopens for cryogenic surgical applications). Along these lines, a retaining area for the reservoir 28 may be included within the device, which may serve to house the reservoir 28 but also permit it to be more easily accessed by the user or by a technician without otherwise disassembling the device. It is also contemplated that the reservoir 28 may be replenishable rather than replicable, for example, via the connection of an external source of inflation fluid to the reservoir, or by other techniques known in the art for replenishing the contents of a reservoir. For example, a replenishment port or conduit may be included. For example, in the case in which helium is used as the inflation fluid, an external helium source may be connected to the reservoir to recharge the reservoir with helium in order to replenish the device. However, according to the first exemplary embodiment illustrated in FIG. 1, it is contemplated that the reservoir 28 will be entirely enclosed and integral within to the rigid elongated member 12, and that the supply inflation fluid contained within the reservoir 28 will continually be recycled between the reservoir 28 and the inflation lumen 24 during the lifetime of the enhanced dilatation device 10, such that there will be no need to ever refill or replace the supply of inflation fluid during the lifetime of the device. In this fashion, it may be seen that one of the principal advantages of the disclosed embodiments is shown, because the device may be entirely self-contained and may operate in entirely the same fashion with the same compactness as conventional electrical powered dilatation device (e.g. "bullet" style vibrators) and may operate without necessitating replacement of consumables or the use of external sources of inflation fluid, such as hand-actuated pumps, etc. which will detract from the convenience and compactness of the device.

The inflation fluid may be, according to the exemplary embodiments, helium gas. Helium gas is the preferred inflation fluid typically utilized in balloon catheters for procedures such as angioplasty and other catheterized enlargement procedures because helium achieves inflation and deflation very rapidly owing to its low molecular weight, and in the case of leaks, helium gas is generally considered benign and is usually eliminated quickly from the body without negative effects. However, it may be seen that other inflation fluids may be used, without necessarily inhibiting the functionality of the enhanced dilatation device 10, including gases other than helium such as air or nitrogen, or liquids such as water or mineral oil, or colloids such as gels. It may further be seen that the inflation fluid may comprise a combination of a gas and a liquid, or in the case of multiple inflation lumens 24 and multiple reservoirs 28, a gas in one lumen/reservoir system, and a liquid in another. It may be appreciated that, for example use of a fluid may more easily enable transmission of vibrations across inflation lumen 24 compared to a gas, which may result in certain qualities of the device being better configured to achieve its intended functionality.

A conduit 30 defining an inflation fluid pathway 32 between the reservoir 28 and the inflation lumen 24 may convey the inflation fluid to and from the reservoir 28 and the inflation lumen 24 during the process of inflation and deflation of the inflation lumen 24. According to the exemplary embodiments in which the reservoir 28 is located within the rigid elongate member 12, it may be seen that the conduit 30 and the inflation fluid pathway 32 it defines may be correspondingly also generally contained within the rigid elongate member 12 except where it fluidly connects to the inflation lumen 24 at the sheath 20. Such embodiments may be seen to be preferred due to the short length of the inflation fluid pathway 32 required, as well as the self-contained nature of the inflation fluid pathway 32 entirely within the device. In comparison to cases in which an external reservoir is used, which may necessitate the use of an exposed, long conduit of a flexible material, this arrangement serves to reduce any probability of wear and damage to the conduit 30 and potential leaks, or restriction and reduction in flow rate along of the inflation fluid pathway 32 due to kinks or bends in the conduit 30. Furthermore, the shorter inflation fluid pathway reduces the energy consumption of the pump 34 necessary to transit the necessary volume of inflation fluid, and allows for more rapid transiting of sufficient volumes of inflation fluid to achieve the necessary aims of the device. The conduit 30 may be formed of any material suitable for use in fluid conduits, including but not limited to tubing materials conventionally used in microfluidics applications such as polytetrafluoroethylene (PTFE), polyetheretherketone (PEEK), and silicone.

A pump 34 is associated with the inflation fluid pathway 32 and is operative to operative to regulate the flow of inflation fluid between the reservoir and the inflation lumen. The pump 34 may any type of pump operative to cause a flow of inflation fluid between the between the reservoir 28 and the inflation lumen 24 at least across any pressure gradient inherent in the construction of the device. According to the preferred embodiment, the pump 34 may be a bidirectional pump operative to transit the inflation fluid in either direction, both to and from the reservoir 28, which may permit rapid inflation and deflation of the inflation lumen 24, while a unidirectional pump in combination with a valve may not necessarily achieve sufficient performance. However, it may be seen that any pump 34 which may be operative to regulate flow between the reservoir 28 and the inflation lumen 24 may be utilized, including pumps which may only be unidirectional, and which rely on a pressure gradient to achieve one of inflation or deflation, depending on the configuration of the device. It may also be seen that two unidirectional pumps may also be utilized, if necessary. Many types of pumps are known in the art which may be of sufficiently compact size with a sufficient flow rate to be contained entirely within a rigid elongated member 12, which are especially well known in the field of microfluidics. As may be readily seen from the above described configuration, when an overall net flow of inflation fluid from the reservoir into the inflation lumen occurs, the inflation lumen will transition to the inflated configuration, and when an overall net flow of inflation fluid from the inflation lumen into reservoir occurs, the inflation lumen will transition to the deflated configuration. In this way, it may be generally seen how the inflatable balloon functionary of the device operates.

A control unit 36 may be seen to control the operation of the pump 34. In the exemplary embodiment, the control unit is contemplated as comprising software or hardware or a combination thereof residing on a microcontroller on an integrated circuit contained within the rigid elongated member 12 and in electronic communication with pump 34. However, it may also be seen that the control unit 36 may be remote from remainder of the enhanced dilatation device 10, such as within a handheld device physically tethered to the remainder of the enhanced dilatation device 10, or partially within the remainder enhanced dilatation device 10 and partially external to it, such as in the case where the control unit may comprise, for example and without limitation, a transponder at the enhanced dilatation device 10 and a remote controller which transmits control instructions to the pump 34. The remote controller may also be, for example, an app on a user's smartphone which connects to the enhanced dilatation device 10 via a wireless receiver 50 within the enhanced dilatation device 10 for receiving control instructions, via conventional wireless protocols such as Bluetooth.

According to one particular contemplated embodiment, the control unit may comprise an accelerometer for detecting motion of the enhanced dilatation device 10. The accelerometer may be, for example, an integrated circuit contained on a circuit board associated with the primary microcontroller of the control unit 36. It is expressly contemplated that according to one important embodiment of the present disclosure, the inflation/deflation cycle of the inflation lumen 24 resulting from the operation of the pump 34 may be operated in response to the detection of motion of the enhanced dilatation device by the accelerometer 38. In particular, it may be preferable for the accelerometer to be configured to detect a direction of motion of the enhanced dilatation device 10 along a longitudinal axis 42 of the rigid elongated member, and for the control unit 36 to be configured to operate the pump so as to cause the inflation lumen 24 to transition to the inflated configuration in response to a detection of motion along the longitudinal axis 42 in the direction of the distal end 16, and to operate the pump so as to cause the inflation lumen 42 to transition to the deflated configuration in response to a detection of motion along the longitudinal axis in the direction of the proximal end 14. In this fashion, it may be seen that once the enhanced dilatation device 10 is positioning within the anus or vagina, inflation of the balloon portion of the device may be automated as a consequence of the device being inserted deeper within the anus or vagina, and likewise deflation of the balloon portion of the device will occur when the device is retracted from the anus or vagina. Furthermore, according to an even more refined embodiment, the accelerometer 38 may be further configured to detect a velocity of the enhanced dilatation device 10 along a longitudinal axis of the rigid elongated member 12, wherein the control unit 36 is further configured to operate the pump 34 so as to control the rate of transition of the inflation lumen 24 between the inflated and deflated configurations as a function of the detected velocity. In this fashion, the balloon portion may be seen to be inflated and deflated in accordance with the measured speed of insertion and retraction of the device, which permits a measure of biofeedback as the device is responsive to the needs of the user at any given time, rather than requiring the user to conform the speed of insertion and retraction to a predefined inflation speed of the device, which may be too fast or too slow for the user's particular preference at any given time. However, it may be seen that other control mechanisms may be utilized, such as predefined speeds of inflation and deflation, which may be adjustable by the user via, for example, a switch, knob, dial or other type of user interface, or non-instantaneous biofeedback mechanisms which may determine an appropriate insertion and retraction speed based upon measurements other than from an accelerometer determining a velocity.

For example, another contemplated exemplary control mechanism, which may be utilized as an alternative to or in addition to one based upon measurements received an accelerometer, may be a control mechanism based upon a pressure sensor 40 positioned within an inflation lumen 24 which may determine a pressure within the inflation lumen 24. As may be readily seen, the control unit 36 may be configured to operate the pump 34 so as to cause the inflation lumen 24 to transition between the inflated and deflated configurations in response to a determination that the pressure within the inflation lumen 24 is above or below one or more predefined pressure levels. Furthermore, it may be seen that control unit 36 may also be configured to operate the pump 34 in response to determinations of pressure changes within the internal lumen 24 with the goal of to maintain a consistent internal volume of the inflation lumen. In this fashion, it may be seen that biofeedback may be taken into consideration, and as the external pressure upon the enhanced dilatation device 10 increases (e.g. due to tensing of the voluntary or involuntary musculature within the pelvic region, the internal volume within the internal lumen 24 will be reduced due to compression of compressible gases within, and thus the device may compensate by flowing more gas into the internal lumen 24 from the reservoir 28 so as to balance the internal and external pressures. In this fashion, a biofeedback effect may be achieved whereby the device responds to biological inputs, which may serve to apply progressive force to musculature, such as those on the pelvic floor, which may otherwise not be adequately stimulated, or which may be overstimulated, if a static device with a rigid surface were to be used. It may be seen that any number of schemes for incorporating sensory feedback, including biofeedback, may be utilized in the presently disclosed embodiments, and that scope and spirit of the disclosure is not to be limited to merely those exemplary control features disclosed herein.

The enhanced dilatation device 10 may also include a stimulatory module adapted to provide additional stimulation. In the exemplary embodiment, the stimulatory module 44 may be, for example but without limitation, a vibrational element for transmitting vibrations to the user during use of the device, as in a conventional vibrating sex toy. For example, it may be preferred for the device to include regions on the shaft portion 18 which are not enclosed by the sheath 20, but rather are formed of a material configured to more readily transmit vibrations produced by the stimulatory module to the user's body during use of the device. It may thus be seen that by positioning certain protruding structural elements on the outside of the device at particular locations, for example, stimulation of certain targeted portions of the user's pelvic region may be realized. Additionally, it may be seen that the stimulatory module 44 may not be limited to a vibrational element, but may include other forms of targeted stimulation, for example, electrical stimulation targeted at the pelvic floor region. Electric pulse devices are well known in the art for use in pelvic floor stimulation, and it may be readily conceived how the presently disclosed device may be modified to provide electrical stimulation in addition to the balloon functionality which represents is the primary functionality of the disclosure herein. It may be seen that any number of schemes for providing further stimulation via one or more stimulation modules 44 known or future invented may be utilized in combination with the presently disclosed embodiments, and that scope and spirit of the disclosure is not meant to be limited to merely those exemplary stimulation schemes disclosed herein.

It is also contemplated that the enhanced dilatation device 10 may be used in connection with an external cover, such as, for example, a condom or similar external barrier, which may, for example, be a custom shaped barrier specifically manufactured for use with the device, and which may be a consumable item requiring replenishment. Along these lines, it is contemplated that use such a barrier so may serve to improve cleanliness and longevity of the device. In this regard, it may be seen that the device may be equipped with certain structural features, for example, at the proximal end 14, which may serve to retain the external barrier on the device during use, so that it is prevented from become unattached from the device.

The enhanced dilatation device 10 may also include a power supply 46 for providing power for the pump 34 and power for the control unit 36 and/or the stimulation module 44 in the case in which the control unit and/or the stimulation module requires a power supply to function. In the exemplary embodiment, the power supply is an internal rechargeable battery which may be connected to an external source of power to recharge, similar to conventional battery powered sex toys. Alternatively, the power supply 46 may comprise one or more replaceable batteries, which again are entirely conventional and known in the art. Perhaps less preferably, the power supply may alternatively be represented by a connection to an external source of power, such as an electrical plug connectable to a residential power outlet. Many other potential forms of motive power are known in the art, and may be utilized as the power supply 46, including but not limited to pneumatic sources of power, such as pneumatic hand pumps (in the case manual control of the pumping elements, for example is desired), or other forms of energy storage other than electrochemically stored energy.

The enhanced dilatation device 10 may also include a pressure release valve 48 for releasing pressure within the internal lumen 24 in the case of malfunction or maltreatment of the device, or in the case the user may wish to manually release pressure from the device to facilitate removal of the device, in the case in which the device may become trapped within the user (e.g. during an uncontrolled vaginismus spasm). For example, the pressure release valve 48 may comprise a relief valve close to the proximal end 14 configured to release inflation fluid in the direction of the proximal end 14 in the case the pressure within the internal lumen 24 exceeds a maximum pressure, via automatic tripping of the relief valve. Such release in the direction of the proximal end 14 may be safer than release of inflation flued elsewhere, as typically the proximal end 14 will not be pointed in the direction of the user's body. Many types of pressure release valves 48 are known in the art, including both manual pressure reduction valves and automatic over-pressure valves, and the scope and spirit of the disclosure is not meant to be limited to merely those exemplary stimulation schemes disclosed herein.

Figure 2:
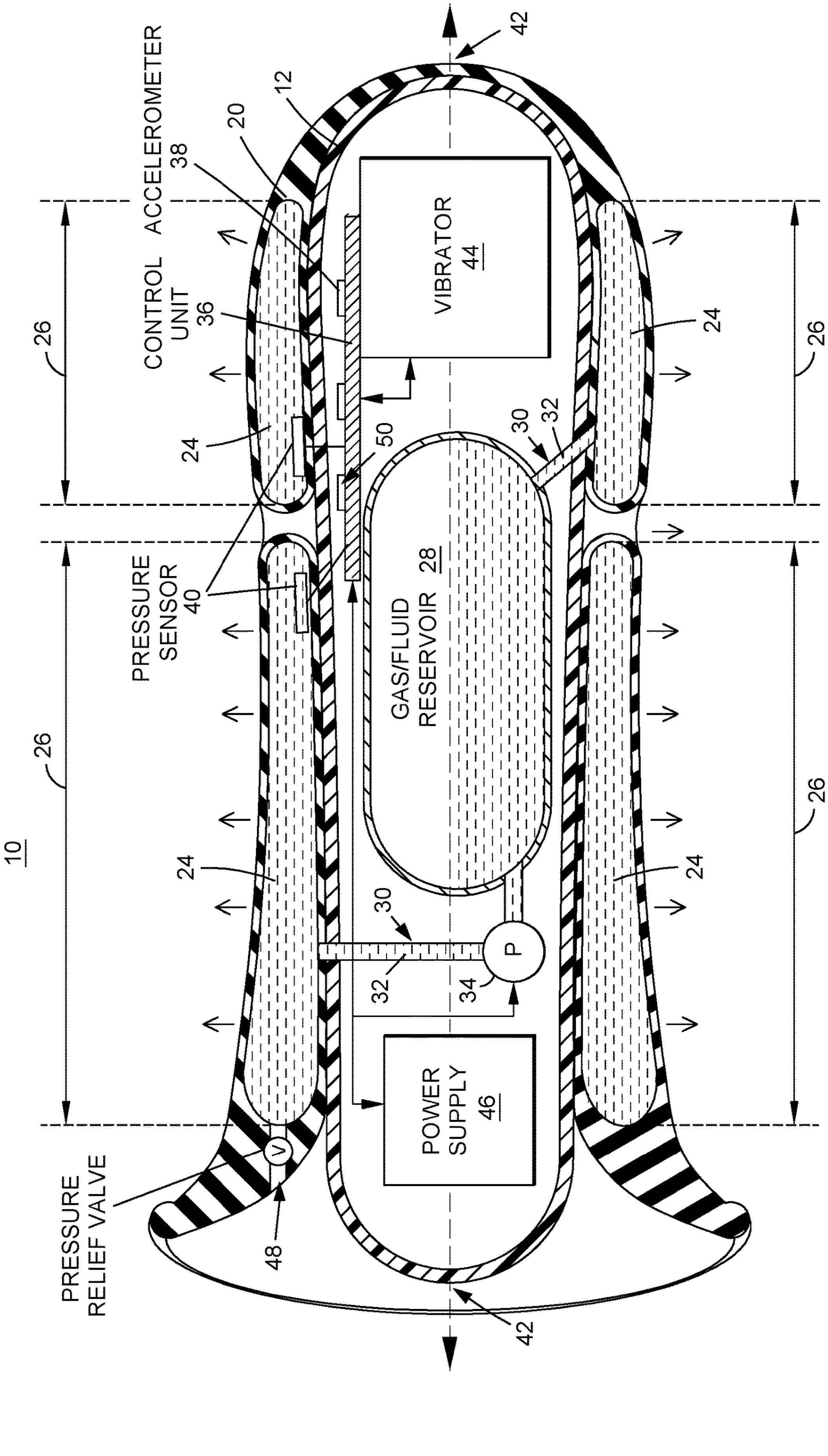
FIG. 2 is a side cutaway view illustrating an enhanced dilatation device according to a second exemplary embodiment of the present disclosure having multiple inflation lumens.

Turning now to FIG. 2, is a side cutaway view illustrating an enhanced dilatation device 10 according to a second exemplary embodiment of the present disclosure having multiple inflation lumens 24 is shown. It may be seen that various different schemes for arrangements of multiple inflation lumens 24 with corresponding multiple inflation portions 26 may be realized, which may or may not include multiple reservoirs 28, conduits 30, and/or pumps 34. For example, it may be seen that, according to the exemplary embodiment, a proximal inflation lumen 24 configured similarly to the embodiment of FIG. 1 described above may be included, while a distal inflation lumen 24 may also be included which is in fluid communication with the reservoir 28 without the presence of a pump to control the flow therebetween, such that the inflation fluid within the distal inflation lumen 24 and will be in equilibrium with the inflation fluid within the reservoir, such that a increase in the volume of inflation fluid added to the proximal inflation lumen 24 via the action of the pump 34 will cause a corresponding reduction of the volume of inflation fluid within the distal inflation lumen 24, and vice versa, resulting in a single pump causing one of the proximal and distal inflation lumens 24 to inflate, while the other correspondingly deflates, which may result in a wave-like pulsating action of the enhanced dilatation device 10 that may result in increased pleasure. Alternatively, more than one reservoir may be provided, and/or a pump may be associated with each conduits 30 between one or more reservoir 24 and each inflation lumens 24 provided, such that each inflation lumen 24 may be independently transitionable between at least a deflated configuration and an inflated configuration, which may permit any number of inflation schemes on top of those already described herein, such inflation schemes not being meant to be limited to merely those exemplary stimulation schemes disclosed herein.

Figure 3:
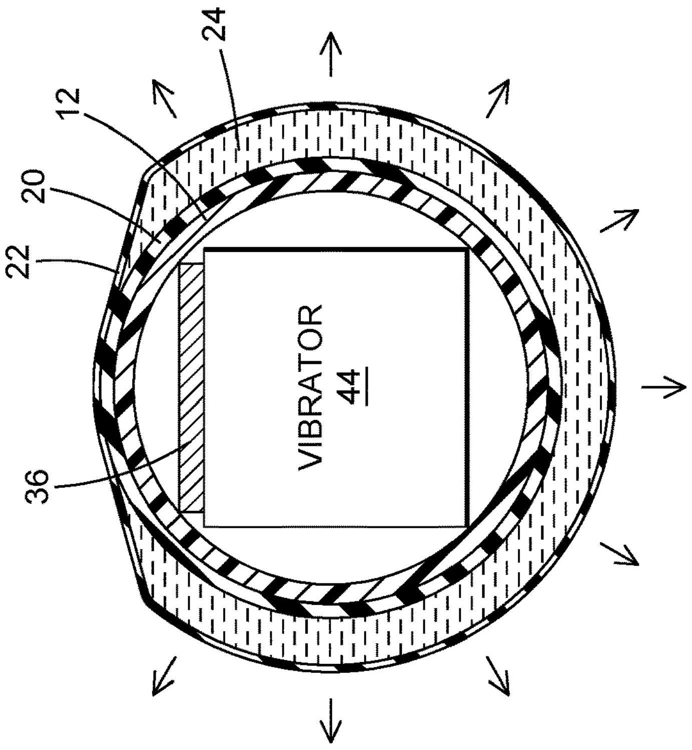
FIG. 3 is a front cross-sectional view illustrating an enhanced dilatation device according to the first exemplary embodiment.

Turning now to FIG. 3, a front cross-sectional view illustrating an enhanced dilatation device according to the first exemplary embodiment of FIG. 1 is shown. As may be seen, in the exemplary embodiment, the inflation lumen 24, when inflated by the operation of the pump, may be seen to cause the inflation portion 26 of the outer surface 22 of the sheath 20 to expand away from the exterior of the shaft region 18 of the rigid elongate member 12. Via use of sheath 20 with consistent cross-sectional characteristics, as illustrated, the inflation portion 26 may be seen to tend to expand outward relatively equidistantly in all directions at which it is located on the shaft region 18. However, as it may here be seen in the illustrated embodiment, by positioning the inflation portion 26 of the sheath 20 along only a portion of the circumference of a circular rigid elongate member 12, a device may be realized in which expansion is focused towards certain directions, while other external portions of the device remain static. Specifically, in the illustrated embodiment, the inflation portion 26 is only positioned over about 320 degrees of a circular rigid elongate member 12, and thus during the inflation/deflation cycling of the device, expansion may only occur at those areas at which the inflation portion 26 is located. Such embodiments may be preferable, for example, where it may be desired to maintain contact of a more rigid region of the device with the user's pelvic region during use of the device regardless of whether the inflation lumen 24 is in the inflated or deflated configuration, such as when a vibratory module is used as the stimulation element 44, as vibrations may not be effectively transmitted across those portions which are covered by the sheath 20, or those portions of the sheath 20 which include an inflation lumen 24. However, it may also be seen that more or less of the cross-sectional exterior of the device may have the inflation portion 26 located over it, up to and including the entire 360 degree periphery. As such, the scope of the disclosed subject matter should not be construed to be limited by the amount or specific areas of the rigid elongate member 12 that are surrounded by the inflation portion 26, and that embodiments with different configurations than those illustrated herein are likewise contemplated.

Figure 4:
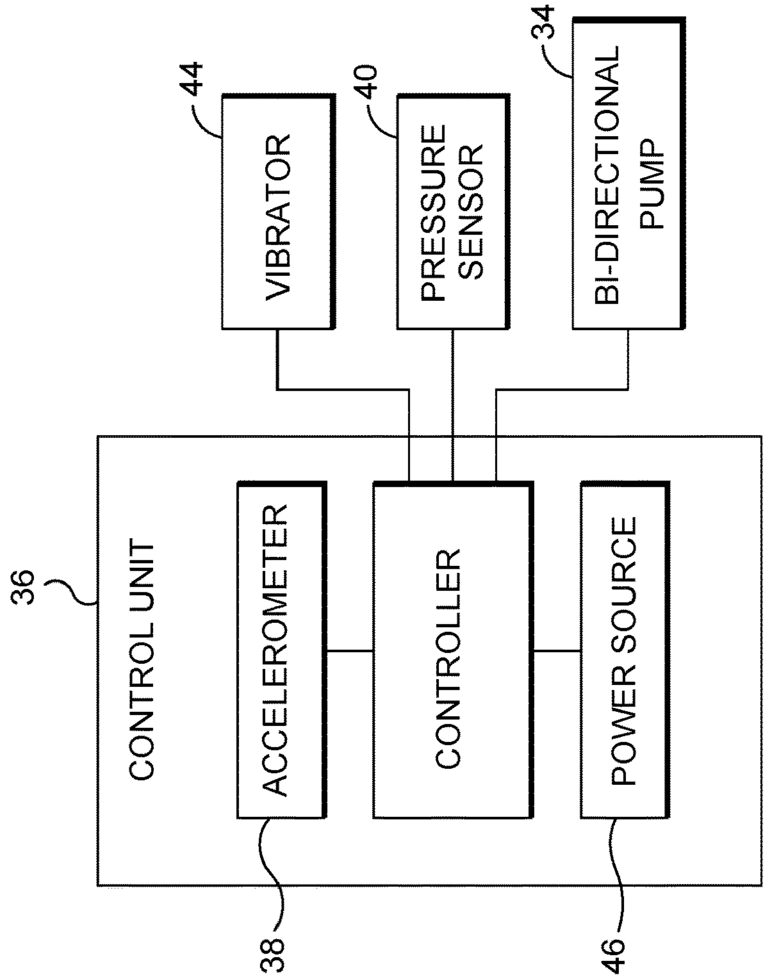
FIG. 4 is schematic diagram showing the electromechanical components of an enhanced dilatation device according to the first exemplary embodiment.

Turning now to FIG. 4, a schematic diagram showing the electromechanical components of an enhanced dilatation device according to the first exemplary embodiment of FIG. 1 is shown. As may be seen, the control unit 36 may include an accelerometer 38 and potentially a power source 46 integrated with (or external to) the control unit, and may include a controller for controlling the bi-directional pump. The control unit 36 may also optionally be in electrical communication with a pressure sensor 40 and/or stimulatory module 44. However, the specific nature of the control unit 36 should not be construed as being limited to merely those exemplary disclosed herein, and the diagram of FIG. 4 is only meant to represent one exemplary way in which a control unit 36 may be organized within an enhanced dilatation device 10.

According to a further embodiment of the contemplated enhanced dilatation device 10 specifically tailored as a therapeutic medical device for treating vaginismus, it is contemplated that the rigid elongate member 12 may have a substantially smaller diameter than that of the illustrated embodiments, which may be generally more suited for use in a device more particularly designed for enhanced sexual stimulation. For example, the rigid elongate member 12 may only have a diameter similar to that of a user's finger or a pencil, but may have a sheath 20 with an inflation lumen 24 configured with walls thicker and more resilient than those of the illustrated embodiments. A vibratory element may or may not be including in order to aid in insertion. In this regard, it may be desirable for the reservoir to be housed in a portion of the device that is not inserted in the user, to aid in improving the form factor for ease of insertion, which may be a region of the proximal end 14 or an external portion connected to the insertable portion via a tether which includes the conduit 30. It may further be seen that in such a configuration, the inflation functionality may be desired to project the inflation portion 26 more rigidly outward, and that to do so, it may be preferred to utilize a liquid rather than a gas as the inflation fluid, in order to better achieve a hydraulic action more resistant to external compressive forces, as liquids are generally incompressible relative to gases. As may be appreciated, for such a configuration, overall speed of inflation/deflation may not be as important as overall rigidity of the inflation portion 26 in order to better counteract any spasms of the user, so by tailoring the device to emphasize those specific features which assist in its functionality, different variations of the herein contemplated devices may naturally be conceived of, designed and/or manufactured by one of skill in the art, and that such variations will still be within the scope of the present disclosure.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the exemplary embodiments.

What is claimed is:

1. An enhanced dilatation device, the enhanced dilatation device comprising:

a rigid elongated member having a proximal end, distal end, and a shaft region therebetween;

a sheath secured to and at least partially enclosing at least a portion of an exterior of the shaft region, the sheath having an outer surface and an inflation lumen, the inflation lumen being transitionable between at least a deflated configuration and an inflated configuration, wherein transitioning of the inflation lumen to the inflated configuration is operative to cause an inflation portion of the outer surface to expand away from the exterior of the shaft region, and wherein transitioning of the inflation lumen to the deflated configuration is operative to cause the inflation portion of the outer surface to retract towards the exterior of the shaft region;

a reservoir operative to contain inflation fluid;

a conduit defining an inflation fluid pathway between the reservoir and the inflation lumen;

a pump associated with the inflation fluid pathway, the pump being operative to regulate a net flow of the inflation fluid between the reservoir and the inflation lumen, the net flow of the inflation fluid from the reservoir into the inflation lumen being associated with the transition of the inflation lumen to the inflated configuration, and the net flow of the inflation fluid from the inflation lumen into the reservoir being associated with the transition of the inflation lumen to the deflated configuration;

a control unit being operative to control operation of at least the pump;

an accelerometer for detecting motion of the enhanced dilation device; and a pressure sensor for determining a pressure within the inflation unit;

wherein the control unit is configured to operate the pump in response to detection of motion by the accelerometer and determination of a pressure within the inflation lumen by the pressure sensor in order to cause transition of the inflation lumen to or from the inflated or deflated configuration;

wherein the accelerometer is configured to detect a direction of motion of the enhanced dilatation device along a longitudinal axis of the rigid elongated member, and wherein the control unit is configured to operate the pump so as to cause the inflation lumen to transition to the inflated configuration in response to a detection of motion along the longitudinal axis in the direction of the distal end, and to operate the pump so as to cause the inflation lumen to transition to the deflated configuration in response to a detection of motion along the longitudinal axis in the direction of the proximal end.

2. The enhanced dilatation device of claim 1, wherein the reservoir is enclosed within the rigid elongated member.

3. The enhanced dilation device of claim 1, wherein the accelerometer is further configured to detect a velocity of the enhanced dilatation device along a longitudinal axis of the rigid elongated member, and wherein the control unit is further configured to operate the pump so as to control the rate of transition of the inflation lumen between the inflated and deflated configurations as a function of the detected velocity.

4. The enhanced dilatation device of claim 1, wherein the control unit is configured to operate the pump so as to cause the inflation lumen to transition between the inflated and deflated configurations in response to a determination that the pressure within the inflation lumen is above or below one or more predefined pressure levels.

5. The enhanced dilatation device of claim 1, wherein the control unit is configured to operate the pump in response to determinations of pressure changes within the inflation lumen in order to maintain a consistent internal volume of the inflation lumen.

6. The enhanced dilatation device of claim 1, further comprising a stimulatory module adapted to intensify sexual stimulation.

7. The enhanced dilatation device of claim 6, wherein the stimulatory module comprises a vibrational element.

8. The enhanced dilatation device of claim 1, further comprising a power source for supplying power to at least the pump.

9. The enhanced dilatation device of claim 8, wherein the power source comprises a rechargeable battery.

10. The enhanced dilatation device of claim 1, further comprising a pressure release valve associated with the inflation lumen.

11. The enhanced dilatation device of claim 1, wherein the inflation fluid comprises helium.

12. The enhanced dilatation device of claim 1, wherein the enhanced dilatation device comprises two or more inflation lumens.

13. The enhanced dilatation device of claim 12, wherein each of the two or more inflation lumens is independently transitionable between at least the deflated configuration and the inflated configuration.

14. The enhanced dilatation device of claim 1, wherein the control unit is configured to receive inputs from a user to control the functionality of the enhanced dilatation device.

15. The enhanced dilatation device of claim 14, wherein the control unit comprises a wireless receiver for permitting the user to wirelessly control the functionality of the enhanced dilatation device.

* * * * *